United States Patent
Wyant

[11] Patent Number: 5,843,065
[45] Date of Patent: Dec. 1, 1998

[54] INCONTINENCE DIAPER WITH OPENING FOR MALE USE

[76] Inventor: James A. Wyant, 1475 32$^{nd}$ Ave., Lachine, Quebec, Canada, H8T 3J1

[21] Appl. No.: 780,897

[22] Filed: Jan. 9, 1997

[51] Int. Cl.$^6$ ..................................................... A61F 13/15
[52] U.S. Cl. ........................................ 604/385.1; 604/395
[58] Field of Search ................................ 604/385.1, 395, 604/386, 387, 396

[56] References Cited

U.S. PATENT DOCUMENTS

| | | | |
|---|---|---|---|
| 2,595,507 | 5/1952 | Beck | 604/395 |
| 3,683,910 | 8/1972 | McKenna . | |
| 4,326,302 | 4/1982 | Lowe . | |
| 4,938,756 | 7/1990 | Salek | 604/378 |
| 4,944,733 | 7/1990 | Casak | 604/385.1 |
| 5,037,413 | 8/1991 | Hague | 604/385.1 |
| 5,057,096 | 10/1991 | Faglione | 604/385.1 |
| 5,207,663 | 5/1993 | McQueen | 604/385.1 |
| 5,383,867 | 1/1995 | Klinger | 604/395 |
| 5,392,467 | 2/1995 | Moretz . | |
| 5,554,149 | 9/1996 | O'Donnell . | |
| 5,569,229 | 10/1996 | Rogers | 604/385.1 |
| 5,618,279 | 4/1997 | Pudlo | 604/385.1 |
| 5,636,387 | 6/1997 | Lundy | 604/385.1 |
| 5,669,902 | 9/1997 | Sivilich | 604/385.1 |

FOREIGN PATENT DOCUMENTS

| | | | |
|---|---|---|---|
| 2224025 | 8/1958 | Australia | 604/396 |
| 2704817 | 8/1978 | Germany | 604/385.1 |

Primary Examiner—Mark O. Polutta
Attorney, Agent, or Firm—Shlesinger Arkwright & Garvey LLP

[57] ABSTRACT

An incontinence diaper having a front section, a back section and a crotch section joining the front and back panels. Fasteners are provided on the upper corners of the front and rear sections for use in joining them together to don the diaper. An absorbent pad is detachably mounted on the inner surface of the front section in the male genital covering area to absorb involuntary urinary discharge. An opening is provided in the front section of the diaper in the male genital covering area. The opening is normally covered by the pad. Moving the pad to uncover the opening allows the diaper wearer to normally urinate through the opening. The opening is preferably shaped to allow a portion of the absorbent pad to be pulled out through the opening to be out of the way during urination.

8 Claims, 2 Drawing Sheets

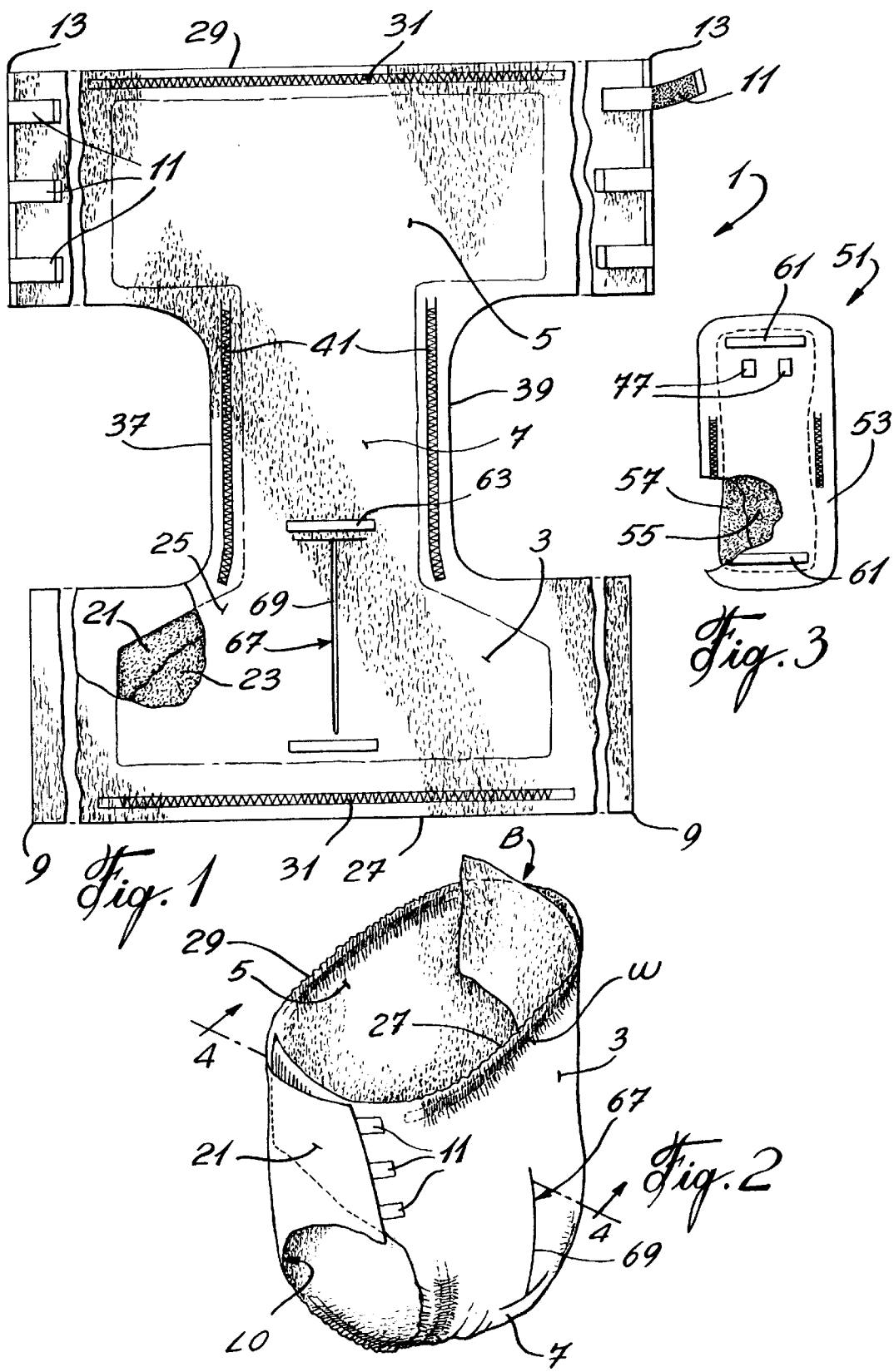

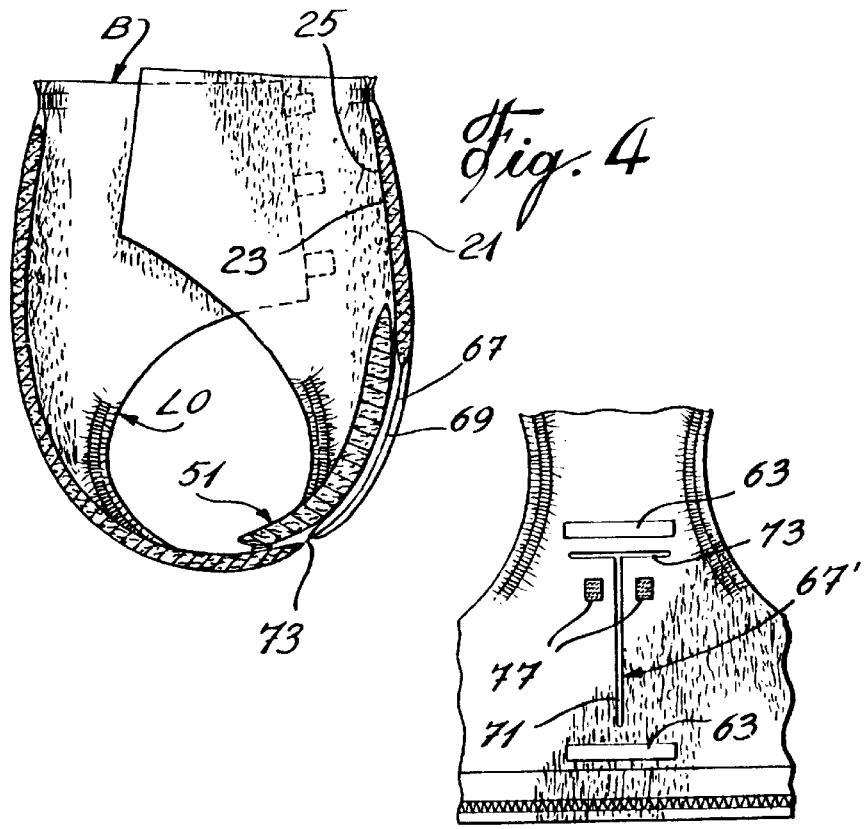
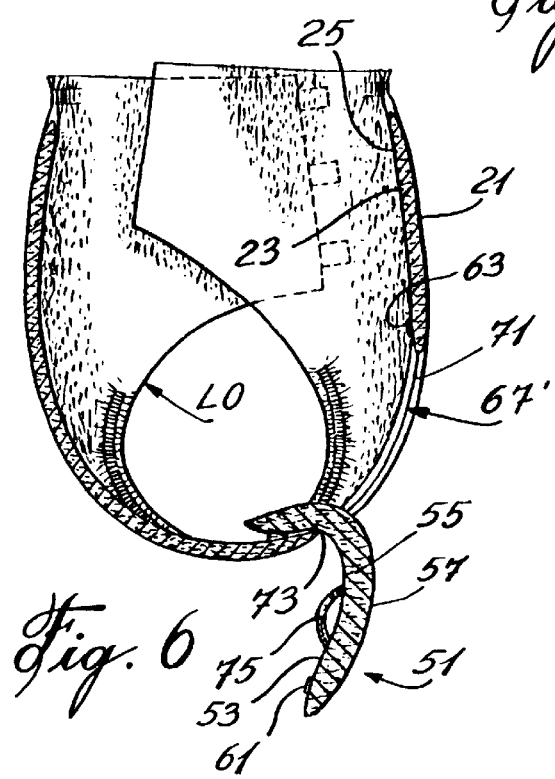

INCONTINENCE DIAPER WITH OPENING FOR MALE USE

BACKGROUND OF THE INVENTION

1. Field of the Invention

This invention is directed toward an improved incontinence diaper.

The invention is more particularly directed toward an improved incontinence diaper for use by males.

2. Description of the Related Art Including Information Disclosure Under CFR SS 1.97–1.99

Incontinence diapers are well known and are designed to be worn by older people who have trouble controlling their bladder and/or their bowels whether they are otherwise well and active or invalid and in bed. The diapers are designed to absorb involuntary urinary leakage and bowel movements. However, when involuntary urinary leakage occurs several times, the entire diaper usually must be replaced, because of smell, even if it is not soiled by bowel movement. This is expensive. To minimize the cost of using these types of diapers, it is known to provide underpants having a replaceable, absorbent, pad at the front of the garment as shown in U.S. Pat. No. 4,326,302, issued Apr. 27, 1982, David R. Cone inventor. When the pad becomes wet through involuntary urinary leakage, it can be easily replaced without having to replace the entire garment. However the pad is located outside the garment and the urinary fluid must pass through the garment to enter the pad. Thus the garment eventually begins to smell and again must be replaced even if not otherwise soiled. In addition, normal urination, through the fly opening in the front of the garment, is awkward because of the location of the pad.

Men are often reluctant to wear incontinence diapers since they normally have no fly opening and thus men cannot easily normally urinate. In an attempt to overcome this problem it is known to provide an incontinence diaper having a slit in the front panel of the diaper through which a man can normally urinate when needed. Such a diaper is shown in U.S. Pat. No. 5,383,867, issued Jan. 24, 1995, Joan Klinger, inventor. The slit is covered by a flap-like member attached to the outside of the front panel the flap member can be peeled away, in part, to uncover the slit to allow normal urination. Once the flap is peeled away however, the diaper does not retain fluid nearly as well as before, even if the flap is adhesively reattached. The adhesive reattachment is not as good as the initial attachment of the flap and as a result, the diaper can leak. In addition the diaper still can become smelly if involuntary leakage occurs necessitating its replacement even if not otherwise soiled.

SUMMARY OF THE INVENTION

It is the purpose of the present invention to provide an improved incontinence diaper that employs a disposable pad to handle the problem of involuntary urinary discharge or leakage thus avoiding the problem of wetting which eventually causes the diaper to smell. It is another purpose of the present invention to provide an improved incontinence diaper that, along with a disposable pad, has a construction providing for normal urination through an opening when desired while minimizing diaper leakage.

In accordance with the present invention there is provided an incontinence diaper having a detachable, disposable absorbent pad that can be fastened on the inner surface of the front panel of the diaper in the male genital covering area. Cooperating fastening means are provided on the pad and panel. When the pad becomes wet from involuntary urinary leaking, it can be easily replaced without having to replace the entire diaper.

Also in accordance with the present invention, there is provided an opening in the front panel of the diaper, normally covered by the pad, that can be used for normal urination by the diaper wearer. The pad normally prevents leakage through the opening, absorbing any involuntary urination because of its normal position. The pad can however be moved to uncover the opening to allow normal urination. The opening is preferably designed to allow the pad to be moved through the opening out of the way of the penis passing through the opening allowing normally unimpeded urination. The pad is pulled back through the opening when normal urination is completed and repositioned in the male genital covering area to be in position to catch involuntary leaking.

The invention is particularly directed toward an incontinence diaper having a front section, a back section and a crotch section joining the front section and back panels. Means are provided on the upper corners of the front and rear sections for use in joining the upper corners of the front and rear sections together to don the diaper. An absorbent pad is detachably mounted on the inner surface of the front section in the male genital covering area to absorb involuntary urinary discharge.

The incontinence diaper of the present invention includes an opening in the front section of the diaper in the male genital covering area. The opening is normally covered by the pad. Moving the pad to uncover the opening allows the diaper wearer to urinate normally through the opening. The opening is preferably shaped to allow a portion of the absorbent pad to be pulled out through the opening to be out of the way during urination.

BRIEF DESCRIPTION OF THE DRAWINGS

FIG. 1 is a plan view, partly broken away, of the incontinence diaper without the absorbent pad;

FIG. 2 is a perspective view of the incontinence diaper formed into a brief;

FIG. 3 is a plan view, partly broken away, of the absorbent pad;

FIG. 4 is a cross section view taken along line 4—4 in FIG. 2;

FIG. 5 is a partial top plan view of another embodiment of the incontinence diaper; and FIG. 6 is a view similar to FIG. 4, of the incontinence diaper shown in FIG. 5, but with the pad moved out through the opening.

DESCRIPTION OF THE PREFERRED EMBODIMENTS

The diaper 1 of the present invention, as shown in FIG. 1, has a front section 3 and a rear section 5 joined by a bottom crotch section 7. The upper corners 13 of the rear section 5 carry straps or adhesive tabs 11 for attaching the front and rear sections 3, 5 together at their upper corners 9, 13 respectively in the form of a brief B, as shown in FIG. 2, when the diaper is worn.

The diaper sections 3, 5 and 7 have an outer, moisture impermeable layer 21; an intermediate, moisture absorbent layer 23 on the inner surface of the outer layer 21; and an inner, moisture permeable layer 25 on the inner surface of the intermediate layer 23 as shown in FIG. 1. At least part of the top edges 27, 29 of the front and rear sections 3, 5 can be elasticized, as shown at 31, to form an elastic waistband W in the brief B when the upper corners 9, 13 of the sections 3, 5 are joined. The side edges 37, 39 of the crotch section 7 can also be elasticized, as shown at 41, to form elasticized leg openings LO in the brief B.

In accordance with the present invention, the diaper is provided with an absorbent pad 51, shown in FIG. 3, that is adapted to be detachably mounted on the central, lower, inner surface of the front section 3 of the diaper as shown in FIG. 4. The pad 51, when mounted, is located in the area of the male wearer's genitals. The pad 51 has a similar construction to the rest of the diaper with an outer, moisture impermeable layer 53; an intermediate, moisture absorbent layer 55; and an inner, moisture permeable layer 57. The outer layer 53 of the pad 51 and the inner layer 25 of the front section 3 have cooperating top and bottom fastening means 61, 63 for detachably connecting the pad 51 to the front section 3 of the diaper with the outer layer of the pad adjacent the inner layer of the front section. The fastening means 61, 63 can comprise male and female strips of Velcro material, or similar hook and eye fastening material. Alternatively, the fastening means can comprise snap fasteners or other type of fasteners.

With the pad 51 mounted in place on the diaper, any involuntary urinary leakage is absorbed by the pad. When the pad becomes too wet, it can easily be replaced without having to replace the diaper by reaching inside the diaper past the elastic waistband on the front of the diaper.

The diaper 1 is also provided with an opening 67 in the front section 3 in the area of the male wearer's genitals as shown in FIGS. 1 and 2. The opening 67 is normally covered by the pad 51 when the pad is in position. The opening 67 can comprise a vertical slit 69 through the layers of material in the front section 3. When the wearer needs to urinate normally, the pad 51 can be removed and wearer can move his penis through the slit 69 to urinate. After urination, the penis is withdrawn back through the slit, and the pad 51 is reattached, all without having to remove the diaper. Instead of removing the pad 51, the wearer could detach one end of the pad from the diaper and fold it out of the way of the slit 69 within the diaper to allow normal urination, the pad being reattached after urination is completed.

Preferably the opening 67' is in the form of an inverted T-shaped slit having a vertical slit length 71 and a bottom, horizontal slit length 73 that crosses the bottom end of the vertical slit length 71 as shown in FIG. 5. The bottom slit length 71 is slightly longer than the width of the pad 51 and is located just above the bottom fastening means 63. In use, when normal urination is required, the pad 51 is detached from the top fastening means 61 by reaching inside the elastic waistband, and then pushed out through the opening 67' to be folded down out of the way as shown in FIG. 6 to allow the penis to be passed through the opening. The cross slit 73 allows the pad 51 to fold flat out of the opening 67'. After urination is completed, the pad 51 is pushed back through the opening 67' and reattached to the top fastening means 61 to cover the opening from the inside, and to be in position for urinary leakage.

If desired, a handling tab 75 can be attached to the outer layer 53 of the pad 51, as shown in FIG. 6, in a position to extend through the vertical slit length 71 of the opening 67'. The tab 75 can be grasped and used to pull the pad out through the opening, after its top end is detached, and to be pushed back in through the opening, without having to handle the absorbent part of the pad which could be wet.

The outer layer of the pad 51 and the inner layer 25 of the front section 3 of the diaper, adjacent the corners formed by the vertical slit length 71 and the cross slit length 73 could also be provided with cooperating fastening means so that the opening 67' remains closed when not in use. Small cooperating Velcro pads 77 could be attached to both the pad and the front panel as shown in FIGS. 3 and 5.

The opening 71 also permits easy access through the diaper for a catheter.

While the invention has been described in diaper form which diaper form is transferred into a brief when in use, the invention could also be applied to a brief. As a brief, the front and rear sections are permanently connected to each other along their sides.

I claim:

1. An incontinence diaper having a front section with upper corners, a back section with upper corners, and a crotch section joining said front and back sections; fastening means provided on said upper corners of said rear section for use in joining said upper corners of said front and rear sections together to don said diaper; a through opening in said front section of said diaper in the male genital covering area for use in normal urination; and an absorbent pad detachably mounted on an inner surface of said front section in the male genital covering area to absorb involuntary urinary discharge, said absorbent pad normally covering said opening in said front section of said diaper when mounted on said inner surface of said front section, said absorbent pad at least partly detachable from said front section to uncover said opening for normal urination.

2. The incontinence diaper as claimed in claim 1, wherein said pad has fastening means at top and bottom portions thereof and cooperating with said fastening means on said inner surface of said front section, said fastening means on said inner surface of said front section located above and below said opening.

3. The incontinence diaper as claimed in claim 2 wherein said opening is shaped to allow a portion of said absorbent pad to be pulled out through said opening to be out of said way during normal urination.

4. The incontinence diaper as claimed in claim 3 wherein said opening is a slit having an inverted t-shape.

5. The incontinence diaper as claimed in claim 4 including a handling tab on said outer surface of said pad accessible through said opening.

6. The incontinence diaper as claimed in claim 1 wherein said opening is shaped to allow a portion of said absorbent pad to be pulled out through the opening so as to be out of the way during normal urination.

7. The incontinence diaper as claimed in claim 6 wherein said opening is a slit having an inverted t-shape.

8. The incontinence diaper as claimed in claim 7 including a handling tab on said outer surface of said pad accessible through said opening.

* * * * *